United States Patent
Soons et al.

(10) Patent No.: US 10,828,593 B2
(45) Date of Patent: Nov. 10, 2020

(54) REMOVAL OF DUST IN UREA FINISHING

(71) Applicant: Stamicarbon B.V., Sittard (NL)

(72) Inventors: Petrus Catharina Gerlach Soons, Sittard (NL); Wilfried Marc Renaat Dirkx, Sittard (NL)

(73) Assignee: Stamicarbon B.V., Sittard (NL)

( * ) Notice: Subject to any disclaimer, the term of this patent is extended or adjusted under 35 U.S.C. 154(b) by 104 days.

(21) Appl. No.: 16/236,097

(22) Filed: Dec. 28, 2018

(65) Prior Publication Data

US 2019/0134554 A1    May 9, 2019

Related U.S. Application Data

(62) Division of application No. 14/902,831, filed as application No. PCT/NL2014/050445 on Jul. 4, 2014, now Pat. No. 10,207,216.

(30) Foreign Application Priority Data

Jul. 5, 2013 (EP) ..................................... 13175399

(51) Int. Cl.
*B01D 47/06* (2006.01)
*B01D 47/10* (2006.01)
*C07C 273/02* (2006.01)

(52) U.S. Cl.
CPC ............. *B01D 47/10* (2013.01); *B01D 47/06* (2013.01); *C07C 273/02* (2013.01)

(58) Field of Classification Search
CPC ........ B01D 47/06; B01D 47/10; C07C 273/02
See application file for complete search history.

(56) References Cited

U.S. PATENT DOCUMENTS

| | | |
|---|---|---|
| 3,615,165 A | 10/1971 | Clement |
| 3,985,523 A | 10/1976 | Kaupas et al. |
| 3,998,626 A | 12/1976 | Baum |
| 4,104,041 A | 8/1978 | Arita et al. |
| 4,127,621 A | 11/1978 | Berst |
| 4,141,701 A | 2/1979 | Ewan |
| 4,217,114 A | 8/1980 | Lagana |
| 4,469,493 A | 9/1984 | Tuovinen |

(Continued)

FOREIGN PATENT DOCUMENTS

| | | |
|---|---|---|
| AU | 679 330 | 6/1997 |
| CA | 1 067 680 | 12/1979 |

(Continued)

OTHER PUBLICATIONS

Machine translation of FR 2600553 from Espacenet accessed Jun. 22, 2020.*

(Continued)

*Primary Examiner* — Cabrena Holecek
(74) *Attorney, Agent, or Firm* — Morrison & Foerster LLP

(57) ABSTRACT

Disclosed is a method for the removal of urea dust from the off-gas of a finishing section of a urea production plant. the method comprises subjecting the off-gas to quenching with water so as to produce quenched off-gas, and subjecting the quenched off-gas to scrubbing using at least one venturi scrubber. As a result, a lower pressure drop over the scrubber is attained, and a more efficient growth of urea particles, facilitating the removal thereof.

13 Claims, 1 Drawing Sheet

(56) References Cited

U.S. PATENT DOCUMENTS

| | | | |
|---|---|---|---|
| 4,507,129 A | 3/1985 | Storen | |
| 4,957,512 A | 9/1990 | Denisov | |
| 5,154,734 A | 10/1992 | Yung | |
| 5,512,085 A | 4/1996 | Schwab | |
| 5,759,233 A * | 6/1998 | Schwab | B01D 47/10 95/8 |
| 5,955,037 A | 9/1999 | Hoist | |
| 6,102,990 A | 8/2000 | Keinanen | |
| 6,383,260 B1 | 5/2002 | Schwab | |
| 6,447,574 B1 | 9/2002 | Frier, Jr. | |
| 6,953,495 B2 | 10/2005 | Schwab | |
| 9,346,007 B2 | 5/2016 | Reddy | |
| 9,751,037 B2 | 9/2017 | Ollila | |
| 2004/0088830 A1 | 5/2004 | Mennen | |
| 2008/0305017 A1 | 12/2008 | Englebert | |
| 2011/0229394 A1 | 9/2011 | Niehues | |
| 2015/0291438 A1 | 10/2015 | Merritt | |
| 2016/0303502 A1 | 10/2016 | Higgins et al. | |

FOREIGN PATENT DOCUMENTS

| | | | |
|---|---|---|---|
| CN | 102000490 | | 4/2011 |
| EP | 0 084 669 | | 8/1983 |
| EP | 0 514 902 | | 11/1992 |
| FR | 2 600 553 | | 12/1987 |
| FR | 2600553 A1 * | 12/1987 | ........... C07C 273/14 |
| WO | WO-2007/076921 | | 7/2007 |
| WO | WO-2007/108008 | | 9/2007 |
| WO | WO-2009/065534 | | 5/2009 |
| WO | WO-2012/106279 | | 8/2012 |

OTHER PUBLICATIONS

Wang et al., Air pollution control project, China University of Mining and Technology Press, Aug. 31, 2012, pp. 118-119.

Cleaning units by PROZAP Engineering, accessed Oct. 29, 2018, http://prozap.com.pl/wp-content/uploads/2017/09/prozap-cleaning-unit-technical-paper-en.pdf (year: 2017).

Communication under Rule 71(3) EPC for EP 14 739 266.6, dated Aug. 18, 2017, 33 pages.

Examination Report No. 2 for standard patent application for AU 2014351079, dated Apr. 26, 2018, 2 pages.

International Search Report and Written Opinion for PCT/NL2014/050445, dated Sep. 22, 2014, 12 pages.

International Search Report for PCT/NL2014/050784, dated Jan. 21, 2015, 4 pages.

* cited by examiner

REMOVAL OF DUST IN UREA FINISHING

CROSS-REFERENCE TO RELATED APPLICATIONS

This Application is a divisional of application Ser. No. 14/902,831 (allowed) having an international filing date of 4 Jul. 2014, which is the national phase of PCT application PCT/NL2014/050445 having an international filing date of 4 Jul. 2014, which claims benefit of European patent application No. 13175399.8 filed 5 Jul. 2013. The contents of the above patent applications are incorporated by reference herein in their entirety.

The invention is in the field of urea production, and pertains to the removal of urea dust from the off-gas associated with the production of solid urea particles (urea finishing). Particularly, the invention pertains to the reduction of the emission of urea dust occurring from such a urea plant finishing section. The invention also pertains to a urea production plant, and to revamping an existing urea production plant.

BACKGROUND OF THE INVENTION

Urea is produced from ammonia and carbon dioxide. Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, and pelletizing.

Prilling used to be the most common method, in which the urea melt is distributed, as droplets, in a prilling tower and whereby the droplets solidify as they fall down. However, the end-product is often desired to have a larger diameter and higher crushing strength than the one resulting from the prilling technique. These drawbacks led to the development of the fluidized bed granulation technique, where the urea melt is sprayed on granules that grow in size as the process continues. Prior to the injection in the granulator, formaldehyde is added to prevent caking and to increase the strength of the end-product.

In order to remove the energy released during crystallization, large amounts of cooling air are fed to the granulation unit. The air that leaves the finishing section contains, inter alia, urea dust. With a view to increased demand for urea production, and increasing legal and environmental requirements as to reduce the level of emissions, it is desired that the urea dust is removed, and according to ever increasing standards.

Over the past several decades the control of air pollution has become a priority concern of society. Many countries have developed highly elaborate regulatory programs aimed at requiring factories, and other major sources of air pollution, to install the best available control technology (BACT) for removing contaminants from gaseous effluent streams released into the atmosphere. The standards for air pollution control are becoming increasingly stringent, so that there is a constant demand for ever more effective pollution control technologies. In addition, the operating costs of running pollution control equipment can be substantial, and so there is also a constant demand for more efficient technologies.

The removal of urea dust is challenging per se, since the amounts of off-gas (mainly air) are enormous, whilst the concentration of urea dust is low. A typical airstream is of the order of 750 000 $Nm^3/h$. A typical concentration of urea dust therein is about 2 wt. %. Further, part of the urea dust is of a submicron size. Satisfying current standards implies the need to remove a major part of this submicron dust.

A further problem is that the large amounts of air needed in urea finishing, results in this part of the production process being a relatively costly effort due to the need for very large extractor fans having a large electricity consumption. Particularly, when the air is subjected to scrubbing in order to reduce the emission of urea dust, and specifically a major part of the submicron dust, into the atmosphere, a relatively large amount of energy is simply lost in the process, as a result of the inevitable pressure drop in the scrubbing device.

One well known type of device for removing contaminants from a gaseous effluent stream is a venturi scrubber. Venturi scrubbers are generally recognized as having the highest fine particle collection efficiency of available scrubbing devices. In a venturi scrubber the effluent gas is forced or drawn through a venturi tube having a narrow "throat" portion. As the air moves through the throat it is accelerated to a high velocity. A scrubbing liquid in the form of droplets, typically of water, is added to the venturi, usually at the throat, and enters the gas flow. The water droplets used are generally many orders of magnitude larger than the contaminant particles to be collected and, as a consequence, accelerate at a different rate through the venturi. The differential acceleration causes interactions between the water droplets and the contaminant particles, such that the contaminant particles are collected by the water droplets. The collection mechanisms involve, primarily, collisions between the particles and the droplets and diffusion of particles to the surface of the droplets. In either case, the particles are captured by the droplets. Depending on the size of the contaminant particles, one or the other of these mechanisms may predominate, with diffusion being the predominant collection mechanism for very small particles, and collision or interception being the predominant mechanism for larger particles. A venturi scrubber can also be efficient at collecting highly soluble gaseous compounds by diffusion. A detailed description of these scrubbing mechanisms is discussed in Chapter 9 of Air Pollution Control Theory, M. Crawford, (McGraw-Hill 1976).

One of the main characteristics of this type of scrubber, is that it causes a larger pressure drop than other scrubbers, the estimated pressure drop required to reach the desired high collection efficiency being about 100 mbar. yet, in view of its suitability for the removal of submicron particles (such as urea dust), it would be desired to make use of a venturi scrubber. It will be understood that using a venturi-type scrubbing device presents a further desire to reduce the inevitable loss of energy associated therewith.

Some background references refer to the use of venturi scrubbing in urea finishing.

FR 2 600 553 relates to removing dust from gases, such as form from urea prilling. The method as described includes subjecting the gas to prewashing, by spraying a liquid into the gas stream, prior to venturi scrubbing. The purpose of the pre-washing step is that no additional scrubbing liquid is added, which would lead to a low pressure drop. I.e., the washing liquid is applied in such a way as to produce droplets that are of a sufficiently large size to wash out small particles.

EP 514 902 relates to a method for the removal of urea dust from the off-gas of a finishing section of a urea production plant. Water is added to act with a venturi scrubber, flowing down by gravity along the walls of the venturi as a film. The gas flowing upward is atomizing the film thereby forming a scrubbing liquid, i.e. with the purpose to form liquid droplets that interact with ammonia, and optionally urea dust, to be removed.

In fact, most venturi scrubbers in use today are "self-atomizing", i.e., the droplets are formed by allowing a liquid to flow into the throat of the venturi where it is atomized by the gas flow. While very simple to implement, this method is not able to produce droplets of very small median diameter.

The primary methods utilized in improving the collection efficiency of a venturi scrubber have been to decrease the size of the throat or to increase the overall rate at which gas flows through the system. Both of these methods increase the differential velocities between the contaminant particles and liquid droplets as they pass through the throat of the venturi. This causes more interactions between particles and droplets to occur, thereby improving contaminant removal. However, increasing the collection efficiency in this manner comes at a cost of significantly higher energy input into the system, thereby resulting in higher operating costs. The extra energy is expended due either to the increased overall flow resistance attributable to the reduced throat diameter, or to the increased overall flow rate through the venturi. In either case, the pressure drop across the venturi is increased and greater pumping capacity is required. Accordingly, heretofore, efforts to increase the fine particle collection efficiency of a venturi scrubber have involved substantial increased energy input into the system.

Of particular concern to those in the field of air pollution control is the collection of "optically active" particles. As used herein, the term "optically active particles" should be understood to mean particles having a diameter in the range of approximately 0.1 to 1.0 microns. In an effort to control these particles, the EPA has recently reduced the "PM 2.5 standards" for the emissions of particles less than 2.5 microns. These and smaller particles are difficult to collect in conventional venturi scrubbers due to their small size. Nonetheless, particles in this size range are currently responsible for the measured emissions.

What is desired is an apparatus and method that permits the efficient and economical scrubbing of fine particles from a large gas flow using a cleansing liquid in a venturi scrubber. Specific needs include reduced scrubbing liquid pumping requirements, lower pressure drop across the venturi, improved scrubber performance, and better control of the pressure drop across the venturi scrubber.

It is now desired to provide a method for treating the off-gas of a urea finishing section in such a way as to effectively remove urea dust. It is further desired to provide a method by which this removal is improved. And, moreover, it is desired to achieve this in a process of improved energy efficiency.

Still another object of the present invention is to provide an air pollution control system which is capable of compensating for variations in the flow through the system.

SUMMARY OF THE INVENTION

In order to better address one or more of the foregoing desires, the invention, in one aspect, presents a method for the removal of urea dust from the off-gas of a finishing section of a urea production plant, the method comprising subjecting the off-gas to quenching with water, particularly so as to produce quenched off-gas having a temperature below about 45° C., and subjecting the quenched off-gas to scrubbing using at least one venturi scrubber.

In another aspect, the invention pertains to a finishing equipment for a urea plant, said finishing equipment comprising a urea finishing device comprising an inlet for liquid urea, an inlet for cooling gas, a collector for solid urea, an outlet for off-gas and at least one venturi scrubber, wherein said outlet for off-gas is in fluid communication (e.g. via a gas flow line) with the venturi scrubber, and wherein a quenching system, such as a spray-quencher, is installed between the urea finishing device and the venturi scrubber.

In a yet another aspect, the invention provides a urea plant comprising a synthesis and recovery section (A); said section being in fluid communication with an evaporation section (B), said evaporation section being in fluid communication with a finishing section (C) and having a gas flow line to a condensation section (E); said finishing section (C) having a gas flow line to a dust scrubbing section (D), wherein the dust scrubbing section comprises at least one venturi scrubber (F), and wherein a quenching system (G) is installed between the finishing section (C) and the venturi scrubber (F), said quenching system being, in fluid communication with the gas flow line between the finishing section (C) and the dust scrubbing section (D).

In a still further aspect, the invention is a method of modifying an existing urea plant, said plant comprising a synthesis and recovery section (A); said section being in fluid communication with an evaporation section (B), said evaporation section being in fluid communication with a finishing section (C) and having a gas flow line to a condensation section (E); said finishing section (C) having a gas flow line to a dust scrubbing section (D), wherein the dust scrubbing section (D) is provided with at least one venturi scrubber, and wherein the method comprises installing a quenching system (G) between the finishing section (C) and the venturi scrubber (F), said quenching system being, in fluid communication with the gas flow line between the finishing section (C) and the dust scrubbing section (D).

DETAILED DESCRIPTION OF THE INVENTION

In a broad sense, the invention is based on the judicious insight to employ quenching of the off-gas of a urea finishing section, in combination with the use of at least one venturi scrubber. Surprisingly, the quenching of the off-gas not only has advantageous effects on the conservation of energy, but also aids in a more efficient removal of urea dust.

It will be understood that liquids used for washing a gas stream, due to the different purpose of the liquid, are not applied in such a way as to induce quenching of the gas. Quenching, as is applied in the present invention, has the purpose of cooling down the gas, preferably to a temperature below about 45° C. and creating a liquid saturation near equilibrium. Preferably, the liquid is sprayed in such a way and consistency that liquid droplets are formed that are so small that the droplets evaporate quickly, and a liquid saturation in the vapour near equilibrium is reached within a short time.

Preferably the quenching stream has a temperature of below 45° C., more preferably below 40° C., most preferably below 35° C. The typical air temperature of the off-gas exiting a finishing section of a urea plant, such as in fluid bed granulation, is about 110° C. After quenching, the temperature is preferably below 45° C. Accordingly, the temperature of the gas stream is lowered by typically more than 50° C., preferably more than 60° C., and most preferably more than 65° C.

Where, in this description, it is spoken of "fluid communication", this refers to any connection between a first part or section of a plant and a second part or section of a plant via which fluids, notably liquids, can flow from the first part of the plant to the second part of the plant. Such fluid communication is typically provided by piping systems, hoses, or other devices well-known to the skilled person for the transportation of fluids.

Where in this description it is spoken of "gas flow lines" this refers to any connection between a first part or section of a plant and a second part or section of a plant via which gas or vapours, notably aqueous vapours, can flow from the first part of the plant to the second part of the plant. Such gas flow lines typically comprise piping systems, or other devices well-known to the skilled person for the transportation of gases, if needed under above or below (vacuum) atmospheric pressures.

Where it is spoken of "venturi scrubber" this can refer to either a single venturi scrubber or a plurality of venturi scrubbers. Further, one or more venturi scrubbers can themselves comprises one or more venturi tubes.

The invention pertains to urea finishing. This part of a urea production process refers to the section where solid urea is obtained.

Figure 1:
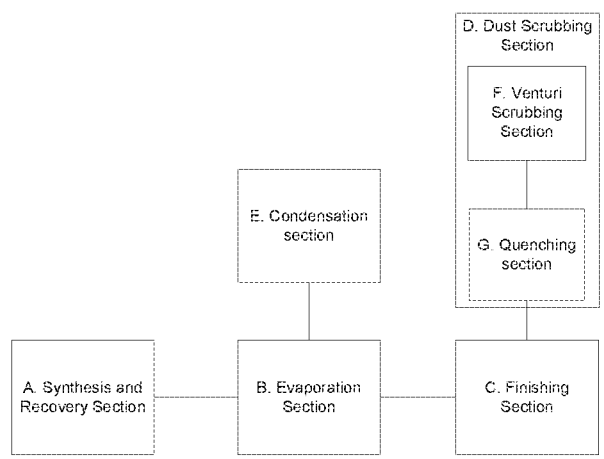
FIG. 1 depicts a block diagram of a urea plant having a finishing section according to the invention.

As an example, a schematic drawing of a plant having a finishing section in accordance with the invention is depicted in FIG. 1. For convenience, parts of the plant discussed below refer to the elements contained in FIG. 1. This does not imply that any plant built in accordance with the invention needs to be in accordance with FIG. 1.

This finishing section, section (C) in FIG. 1, may be a prilling tower, granulation section, pelletizing section, or a section or equipment based on any other finishing technique. A granulation section may be a fluidized bed-granulation, or a drum granulation, or a pan-granulation, or any other similar and known granulation device. The main function of this finishing section is to transfer a urea melt, as obtained from urea synthesis, into a stream of solidified particles. These solidified particles, usually called 'prills' or 'granules' is the main product stream from the urea plant. In any event, to transfer the urea from the liquid phase into the solid phase, the heat of crystallization has to be removed. Moreover, usually some additional heat is removed from the solidified urea particles, in order to cool them to a temperature that is suitable for further processing and handling, including safe and comfortable storage and transport of this final product. The resulting total removal of heat in the finishing section is usually done in two ways: (i) by evaporation of water. This water enters the finishing section either as part of the urea melt, or is sprayed as liquid water at an appropriate place in the finishing process; (ii) by cooling with air. Usually most of the crystallization/cooling heat is removed by cooling with air. The cooling air, by nature of the cooling process, leaves the finishing section at an increased temperature. Usually an amount of air equal to 3-30 kg of air per kg of final solidified product is applied, preferably 3-10 kg. This is the typical off-gas of the finishing section of a urea production plant.

In the finishing section (C), the air comes into direct contact with the urea melt and with the solidified urea particles. This inadvertently leads to some contamination of the air with some urea dust, and ammonia. Depending on the nature of the finishing section (prilling/granulation, type of granulation, conditions selected in granulation), the amount of dust present in the air may vary widely, values being in the range of 0.05% to 10% by weight (with respect to the final product flow) having been observed. For a finishing section based on granulation, the amount of dust more typically is in a range of from 2% to 8% by weight. This presence of dust in the off-gas usually makes a dust removal system (D) required, either for environmental or from economical considerations, before the air can be vented back into the atmosphere.

In the dust scrubbing section (D), dust scrubbing is usually done using a circulating urea solution as a washing agent. On top of this also fresh water scrubbing usually is applied. In the dust scrubbing section D a purge flow of urea solution is obtained. This purge flow usually has a concentration of 10-60% (by wt.) of urea. In order to reprocess the urea present in this purge flow, the purge flow is returned to the evaporation section (B), where it is further concentrated and then recycled to the finishing section (C). Cleaned air is vented from the dust scrubbing into the atmosphere.

According to the invention, in one aspect, a method is provided for the removal of urea dust from the off-gas of a finishing section of a urea production plant. The method comprises subjecting the off-gas to quenching with water so as to produce quenched off-gas, and subjecting the quenched off-gas to scrubbing using at least one venturi scrubber.

Quenching refers to adding water to the off-gas. This is generally done by one or more quenchers, i.e. devices that serve to introduce water into the gas stream. This introduction will generally be done in such a way that the water is well-dispersed into the gas. Preferably, the water is introduced into the gas by spraying it into the gas flow line between the finishing section and the dust scrubbing section. This can be done by spraying liquid into a duct just preceding the dust scrubbing section. It can also be a separate chamber or tower equipped with a spray system. Spray systems, suitable atomization nozzles, and the like, are known to the skilled person. Preferably, the liquid is sprayed in such a way and consistency that liquid droplets are formed that are so small that the droplets evaporate quickly and a liquid saturation in the vapour near equilibrium is reached within a short time.

A quench section employing spray quenchers will preferably comprise (a) a section in which the gas to be quenched is cooled by the introduction (e.g. injection) and evaporation of water; (b) a dust collection basin, serving to collect dust stripped from the gas; (c) a sprayer system, mounted on a cylindrical portion and consisting of lances equipped with injection nozzles, and a water supply system with pumps.

The off-gas (or "gaseous effluent") coming from the finishing section, e.g. from a prilling tower of fluid bed granulator, is intended to include effluent streams that have liquid or solid particulate material entrained therein, including vapours which may condense as the effluent stream is cooled.

In the quench zone, the gaseous effluent is cooled to a much lower temperature, preferably below about 45° C. Many methods of cooling a hot effluent gas flow are known to those skilled in the art.

A preferred method for use in the invention involves spraying a cooling liquid such as water, into the gas through nozzles. Without wishing to be bound by theory, the inventors believe that spray-quenching contributes to the efficient removal of dust, by allowing water to interact with dust particles.

This is an unexpected benefit of spray-quenching. In the art, not related to urea but, e.g., to flue gas, cooling of a gaseous effluent has an effect in supersaturated systems. Therein, cooling the effluent causes condensable vapours in the effluent stream to undergo phase transition. Condensation of these vapours will naturally occur around particles in the effluent stream which serve as nucleation points. Pre-cooling the effluent stream is, thus, useful for two reasons. First condensable contaminants are transformed to the liquid phase and are thereby more easily removed from the effluent. Second, the nucleation process increases the size of pre-existing particles in the effluent, thereby making it easier to remove them.

The removal of the larger particles by quenching prevents the larger particles from competing with the submicron particles as nucleation sites. As mentioned above, it is desirable that the submicron particles increase in size due to condensation so that they are easier to remove from the effluent flow.

A problem with the gaseous effluent treated in the invention, i.e. the off-gas of a finishing section of a urea plant, is that it is in a subsaturated state. As the sole condensable vapours, the off-gas contains a limited amount of water. As a result, it should be cooled down to much lower values than achievable by quenching in order to have water condensate as desired.

The fact that, by spray quenching, in the subsaturated urea finishing off-gas an interaction with water is capable of contributing to the effective removal of dust, thus is surprising. Without wishing to be bound by theory, the inventors believe that this effect is caused by evaporation of the sprayed water. This causes a lowering of the temperature, and an increase of the amount of water in the gas-phase. As a result, an interaction of water with submicron dust becomes possible.

A venturi scrubber is a known device, designed to effectively use the energy from an inlet gas stream to atomize a liquid that is used to scrub the gas stream. A venturi scrubber consists of three sections: a converging section, a throat section, and a diverging section. The inlet gas stream enters the converging section and, as the area decreases, gas velocity increases. Liquid is introduced either at the throat or at the entrance to the converging section.

The inlet gas, forced to move at extremely high velocities in the small throat section, shears the liquid from its walls, producing an enormous number of very tiny droplets. Particle and gas removal occur in the throat section as the inlet gas stream mixes with a fog of tiny liquid droplets. The inlet stream then exits through the diverging section, where it is forced to slow down. Venturis can be used to collect both particulate and gaseous pollutants, but they are more effective in removing particles than gaseous pollutants.

Hence, a venturi scrubber by its nature is a suitable scrubbing device for the removal of urea dust from a gas stream. However, the use of venturi scrubbers for this purpose, meets with limitations due to the relatively high operational costs associated with it. This particularly refers to the inevitable pressure drop occurring in a venturi scrubber, as a result of which a relatively high amount of energy input goes lost. The latter has adverse consequences for the energy consumption of the urea plant, and this is a concern both from an economical and an environmental perspective. Particularly the latter would mean that one trades one drawback (air pollution) for another (energy consumption).

In accordance with the invention, the step of quenching the off-gas from a urea finishing section, before the gas is subjected to venturi scrubbing, has an unexpected dual effect.

On the one hand, the quenching of the off-gas from the urea finishing section results in lowering the temperature of the off-gas entering the venturi scrubber. This lowering of temperature leads to a reduction of the gas volume and hence to a lowering of pressure drop. This, in turn, results in a higher percentage of energy conserved in the plant.

On the other hand, said quenching results in the presence of large amounts of water droplets in the vapour phase, and hence to the the presence of vapour in the airflow (off-gas) wherein urea dust is present. Based on theory, this would not have been expected to bring about significant effects. In the art it is acknowledged that aerosol-particles (in the sub-micron and micron size range as is typical for urea dust) grow due to condensation of water on them from supersaturated gas that surrounds such particles. If the gas surrounding the aerosols/particles is saturated or sub-saturated, but not supersaturated, there is no growth or even negative growth of water from the wet surface of the aerosol-particle. As a result, the particle remains the same size or even evaporation from the surface of the particle occurs. The general belief is that the degree of supersaturation (known as a factor S) needs to be larger than unity (1) to obtain condensation of water on aerosols, which is imperative to obtain growth of particles. Throughout the art on removing sub-micron dust particles, it is acknowledged that effective removal requires an atmosphere in which water vapour is present in a supersaturated state.

Specifically in the art of urea finishing, such as in urea-granulation technology, it is recognized that it is impossible, in practice, to obtain a supersaturated gas-stream downstream of the finishing step. This can be explained with reference to the large amount of relatively dry air, and thus low presence of amounts of water, that are naturally present in the off-gas from urea finishing (e.g. from the granulator). In fact, the system initially (in the finishing section) starts from almost zero saturation, i.e., too strongly an undersaturated situation to reach a level of saturation, let alone supersaturation. Furthermore considering the following:

the large amount of liquid droplets that are present acting as seeds for condensation;
the short residence time in the quenching section;
the thermodynamic limitations (required energy for evaporation of liquid water into vaporized water is not present);
the start of the system is strongly undersaturated;

in practice no supersaturated state can be reached in the quenching section.

However, against the art-recognized beliefs, the inventor found that, surprisingly, a relatively large amount of condensation of water on the micron-size and sub-micron size urea particles takes place upon quenching. This leads to a significant growth of the micron-size and sub-micron-size particles. This growth of the sub-micron size particles due to condensation of water on them, leads to a significantly larger particle size which makes the particles much easier to be collected/caught at acceptable pressure drops in the venturi section downstream of the quenching section.

Overall, therefore, the method of the invention brings about a judicious combination of technical measures, that synergistically co-operate to meet the aforementioned desires in the art. Particularly, the more efficient removal of urea dust means that the venturi scrubber can be operated at a lower pressure drop. Moreover, the quenching of the off-gas before it enters the venturi scrubber, results in a smaller volume of gas, and therefore a lower pressure drop. Or, put otherwise, the desire to reduce the pressure drop over the venturi scrubber, which is done by cooling the air entering the venturi, can be realized by another (unexpected) effect of the quenching method used for said cooling, viz. the urea particle growth, and hence more efficient removal thereof. Overall, the invention leads to very good collection/washing efficiencies for sub-micron urea particles, at a moderate pressure drop, allowing the use of smaller equipment, and consuming less power. The latter, on the one hand, is because of the lower pressure drop, on the other a lesser requirement for pressure drop because of the higher efficiency due to the unexpected effect of quenching.

The invention also pertains to the equipment for carrying out the above-described method. This refers to a finishing equipment for a urea plant. Therein a urea finishing device is present comprising the appropriate attributes to perform its function. These attributes are known to the skilled person, and generally include an inlet for liquid urea, an inlet for cooling gas, a collector for solid urea (typically: urea particles, preferably granules), and an outlet for off-gas. The outlet for off-gas is in fluid communication (typically via a gas flow line) with the inlet of at least one venturi scrubber (the inlet being into the converging section). According to the invention, a quenching system, preferably a spray quencher, is installed between the urea finishing device and the venturi scrubber. It will be understood that the quenching system is installed in such a way that water sprayed therefrom enters the gas stream that flows from the outlet of the finishing section and the inlet of the venturi scrubber.

In a preferred embodiment, the dust removal system comprises a plurality of venturi scrubbers, operated in parallel. Preferably, the dust removal system is so designed that these parallel venturi tubes can be operated independently of each other, i.e. the number of venturi tubes used at the same time, can be adapted during the process as desired. A preferred system is that provided by Envirocare.

Envirocare scrubbers consist of a quenching section, downstream of which a so-called MMV-section (micro-mist Venturi) is installed. The MMV-section consists of multiple parallel venturis. In the MMV-section large quantities of liquid are sprayed in the throat of the venturis co-current with the gas-flow through single phase nozzles, creating a consistent and adjustable liquid droplet-size, typically in a range of from 50 µm to 700 µm. The liquid droplet size is one of the parameters that can be used to control the efficiency of dust-removal In the Venturi, intimate contact between particulate matter and waterdroplets takes place. Multiple passages between particulate matter and water droplets takes place because initially the water droplets are accelerated by the gas-flow (and thus have lower velocity than the gas-flow), while in the latter part of the venturi-tube, due to expansion, the gas velocity decreases while the droplets are at velocity and maintain their velocity due to inertia (now liquid droplets have a higher velocity than gas-flow).

Counter-currently with the gas-flow the so-called throat spray takes place that controls the pressure drop over the venturi-section. In this way fluctuations in gas-flow can be accommodated at more or less constant efficiency.

So, while in a standard venturi water-droplets (or, rather, water-fragments) are created by shear-forces, in the Envirocare concept a specific size (and shape) of water droplets is created. This ensures a good and efficient distribution of water and thus good washing. As a result, while in a standard venturi-scrubber, the mixing of water is depending of the quality of shear, the flow-patterns inside the throat and the diverging zone, in the Envirocare concept the mixing is controlled.

While a standard venturi scrubber's collection efficiency is strongly depending on fluctuations in gas-flow (thus fluctuations in pressure drop), the Envirocare scrubber controls the pressure drop by the throat spray.

The electricity consumption for a granulation section of a urea plant, utilizing a high efficiency venturi scrubber is estimated at 52 KWh/ton. Utilizing an Envirocare scrubber, with quenching, the electricity consumption of the granulation section of a urea plant goes to 47 kWh/ton.

Venturi scrubbing relies on the differential velocity between scrubbing droplets and contaminant particles. The gaseous effluent and the spray droplets both enter the inlet cone of the venturi at relatively low velocities. Differential velocities are achieved primarily as the particles and droplets undergo acceleration through the throat of the venturi. Normally, the contaminant particulates, being much smaller and having much less mass, rapidly accelerate to attain the velocity of the surrounding gas in a very short distance. On the other hand, the scrubbing liquid droplets are normally much larger and more massive, so that it takes them much longer to attain the velocity of the gas stream. Typically, these droplets will not reach this ultimate velocity until the end of the throat or beyond the end of the throat. Since it is the velocity differential which causes scrubbing, once the droplets and particles reach the same velocity the number of interactions between the two will reduce to the point of insignificance, and no further scrubbing will occur.

The scrubber contains a plurality of venturis (venturi tubes), housed in the scrubber vessel. All of the venturis are substantially the same, and are of a similar design. The advantage of using multiple venturis is that it permits a more compact overall design and reduces the size of the individual nozzles. Smaller nozzles are better able to produce the fine scrubbing droplets needed for efficiency. The number of venturi tubes affects efficiency and pressure drop.

The scrubber design used in the invention is particularly well suited to retrofit existing pollution control equipment to improve scrubbing efficiency and lower operating costs. To retrofit an existing low energy impingement scrubber, multiple venturis may be housed in the impingement chamber or in an extension to the chamber after one or more impingement plates.

A quenching section is disposed in the gas duct upstream of a MMV scrubbing tower and a scrubbing solution is provided at that section for quenching and cooling of the gas effluent coming from a Fluid Bed Granulator (or other finishing section). The quench section performs the function of adiabatically humidifying or quenching the gas stream from approximately 100° C. to a temperature of about 50° C. using a scrubber solution coming from the venturi scrubber vessel.

The invention also pertains to a urea plant comprising a finishing section as described above. More particularly, the urea plant of the invention, as illustrated in the example of FIG. 1, comprises a synthesis and recovery section (A); which is in fluid communication with an evaporation section (B). The evaporation section is in fluid communication with a finishing section (C), and has a gas flow line to a condensation section (E). The finishing section (C) has a gas flow line to a dust scrubbing section (D). In accordance with the invention, the dust scrubbing section comprises at least one venturi scrubber (F), and a quenching system, preferably a spray-quencher (G). The quenching system is installed between the finishing section (C) and the venturi scrubber (F), and is in fluid communication with the gas flow line between the finishing section (C) and the dust scrubbing section (D). Preferably, a plurality of venturi scrubbers is employed as outlined above. It will be understood that any desired number of venturis is in fluid communication (typically via a gas flow line) with the gas outlet of the finishing section.

The invention is applicable to the construction of new urea plants ("grass root" plants) as well as in revamping existing urea plants.

It will be understood that a new plant according to the invention can just be built in conformity with the above. In revamping existing plants, the invention pertains to a method of modifying an existing urea plant, in such a way as to ensure that the plant has a dust scrubbing section provided with at least one scrubber, and wherein a quenching system is installed between the finishing section and the scrubber and the scrubber is replaced or modified to a venturi scrubber. In another embodiment, in addition to one or more venturi scrubbers, an additional acid scrubber can be used to improve the removal of ammonia. This scrubber is preferably placed downstream of the one or more venturi scrubbers.

The invention is not limited to any particular urea production process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapour phase leaves the stripper at the top part. The vapour leaving said stripper contains ammonia, carbon dioxide and a small amount of water. Said vapour is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapour is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapour containing non-condensed ammonia and carbon dioxide is sent to a scrubbing section operating at a similar pressure as the reactor. In that scrubbing section the ammonia and carbon dioxide is scrubbed from the inert vapour. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

Other processes and plants include those that are based on technology such as the HEC process developed by Urea Casale, the ACES process developed by Toyo Engineering Corporation and the process developed by Snamprogetti. All of these processes, and others, may be used preceding the urea finishing method of the invention.

Urea finishing techniques, such as prilling and granulation, are known to the skilled person. Reference is made to, e.g., Ullmann's Encyclopedia of Industrial Chemistry, 2010, chapter 4.5. on urea.

The invention will be further illustrated hereinafter with reference to the Example below. The Example is not intended to limit the invention.

Example

Figure 2:
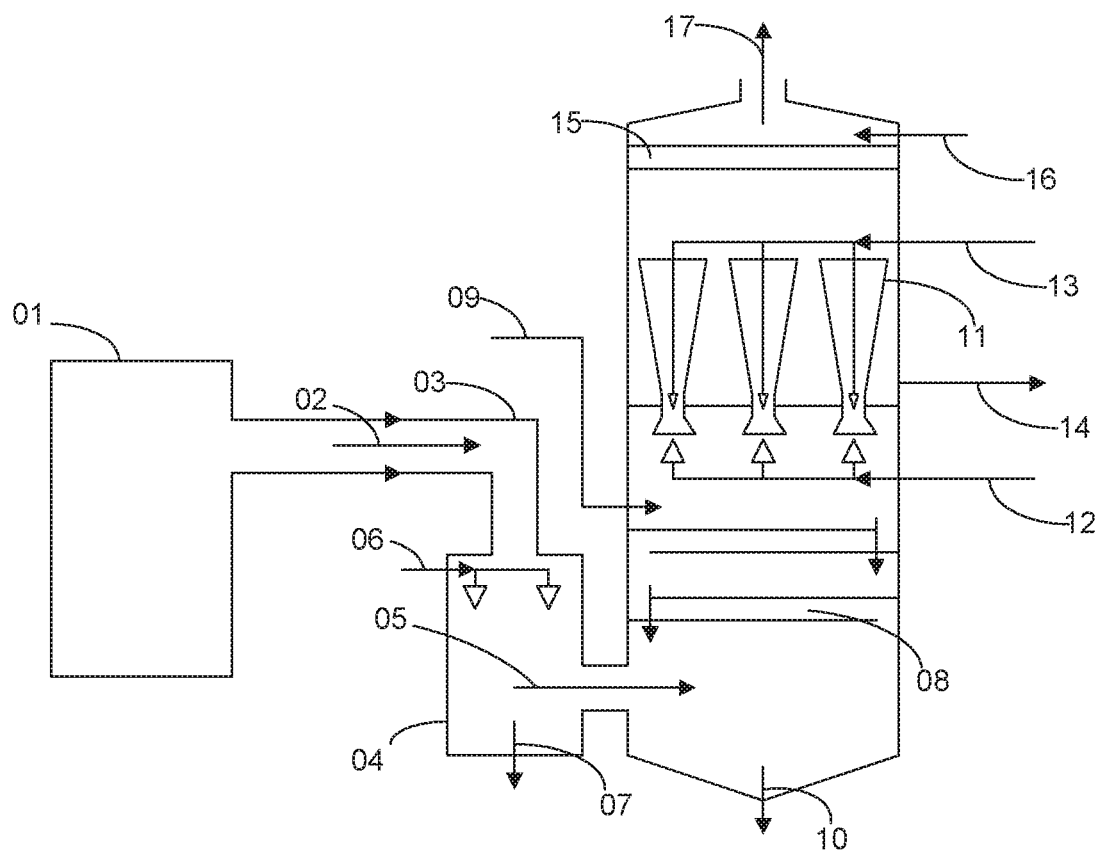
FIG. 2 shows a schematic drawing of a dust scrubbing system used in the present invention.

This Example refers to FIG. 2, which shows an exemplary dust scrubbing system of the present invention. An off-gas stream laden with entrained urea dust-particles is generated by a finishing section 01. From the finishing section 01, the off-gas stream 02 is delivered to the dust-scrubbing system though a duct 03.

The dust scrubbing system removes urea particles from the off-gas stream 02 in two stages. In a first scrubbing stage, the so-called quenching stage, the off-gas 02 flows though the quenching section 04, where the majority of large urea particles are removed from the off-gas, resulting in a partially scrubbed off-gas flow effluent as flow 05.

Furthermore in the quenching section 04, the off-gas 02 is cooled and moistened with water. It is preferred that the gas in flow 05 is near to moisture saturation.

For the purposes of cooling, saturating and scrubbing, a liquid flow 06 is introduced through nozzles in the quenching section 04. The liquid flow 06 can either be a clean water flow or a urea-solution in water. The formed urea solution 07 is discharged from the quenching section. This urea solution 07 can either be discharged but can also be partly recycled to stream 06.

The following stage 08 is optional for the application in urea. The stage 08 comprises of a washing stage in which condensed vapours and size-enlarged micron and sub-micron particles for a part can be removed from the off-gas stream. For this purpose a washing liquid 09 is introduced to the top-part of the washing stage, during percolating down through the washing stage 08, some collection of particles takes place. The formed urea solution 10 is discharged from this section 08. The urea solution 10 will partly be recycled as washing liquid.

The off-gas stream flows to an MMV-section 11 (i.e. a Micro-Mist Venturi). The off-gas flows through the venturis 11. Below each venturi a liquid-spray nozzle co-currently sprays liquid-droplets in the venturis, the so-called MMV-spray 12. The liquid for the MMV-spray can either be clean water or a urea solution in water.

Counter currently to the off-gas flow, the so-called throat-spray takes place via nozzles inside the throat of the venturis. The throat-spray liquid 13 can either be water or a solution of urea in water.

The wash-water from the MMV-stage containing the dissolved urea is discharged as a liquid stream 14. Downstream of the MMV-section, a demister-section 15 is installed to capture droplets and/or wetted particles. The demister is wetted by make-up water flow 16. The cleaned off-gas 17 stream leaves the dust-scrubber.

The invention claimed is:

1. A finishing equipment for a urea plant, said finishing equipment comprising a quenching system, one or more venturi scrubbers and a urea finishing device,
    wherein the urea finishing device comprises an inlet for liquid urea, an inlet for cooling gas, a collector for solid urea, and an outlet for off-gas,
    wherein said quenching system comprises an inlet that is connected with said outlet for off-gas of the urea finishing device and comprises an outlet for quenched off-gas, and
    wherein the one or more venturi scrubbers comprise(s) an inlet which is connected with said outlet for quenched off-gas.

2. A finishing equipment according to claim 1, wherein the urea finishing device is a fluid bed granulation unit.

3. A finishing equipment according to claim 1, wherein said venturi scrubber comprises a plurality of venturi tubes which are arranged in parallel.

4. A finishing equipment according to claim 1, further comprising an acid scrubber for the removal of ammonia, which is arranged downstream of the one or more venturi scrubbers.

5. A finishing equipment according to claim 1, wherein the one or more venturi scrubbers are of the micro mist venturi (MMV) type.

6. The finishing equipment according to claim 1,
    wherein the at least one venturi scrubber is configured for subjecting the quenched off-gas to scrubbing to give scrubbed gas,
    wherein said venturi scrubber comprises a throat, a converging section, and an entrance to said converging section,
    wherein said venturi scrubber is furthermore configured for adding a scrubbing liquid to the venturi scrubber at said throat or at said entrance such that said added scrubbing liquid enters the quenched off-gas
    wherein said quenching system is configured for subjecting the off-gas to quenching with water optionally in the form of an aqueous solution so as to produce quenched off-gas,
    wherein the quenching system is arranged upstream of the venturi scrubber such that the quenching takes place before the off-gas enters the venturi scrubber, and
    wherein the finishing equipment further comprises a washing section comprising an inlet for a washing liquid and configured for percolation of the washing liquid down through said washing section thereby collecting particles from said quenched off-gas stream.

7. A urea plant comprising a synthesis and recovery section, an evaporation section, a condensation section, a finishing section, a dust scrubbing section, and a quenching system,
    wherein said synthesis and recovery section is in fluid communication with said evaporation section,
    wherein said evaporation section is in fluid communication with said finishing section and has a gas flow line to the condensation section; and
    wherein said finishing section has a gas flow line to said dust scrubbing section, wherein the dust scrubbing section comprises at least one venturi scrubber,
    wherein said finishing section comprises a urea finishing device comprising an inlet for liquid urea, an inlet for cooling gas, a collector for solid urea, and an outlet for off-gas,
    wherein said quenching system comprises an inlet that is connected with said outlet for off-gas of the urea finishing device and comprises an outlet for quenched off-gas, and
    wherein the at least venturi scrubber comprises an inlet which is connected with said outlet for quenched off-gas.

8. The urea plant according to claim 7,
    wherein the at least one venturi scrubber is configured for subjecting the quenched off-gas to scrubbing to give scrubbed gas,
    wherein said venturi scrubber comprises a throat, a converging section, and an entrance to said converging section,
    wherein said venturi scrubber is furthermore configured for adding a scrubbing liquid to the venturi scrubber at said throat or at said entrance such that said added scrubbing liquid enters the quenched off-gas
    wherein said quenching system is configured for subjecting the off-gas to quenching with water optionally in the form of an aqueous solution so as to produce quenched off-gas,
    wherein the quenching system is arranged upstream of the venturi scrubber such that the quenching takes place before the off-gas enters the venturi scrubber, and
    wherein the finishing equipment further comprises a washing section comprising an inlet for a washing liquid and configured for percolation of the washing liquid down through said washing section thereby collecting particles from said quenched off-gas stream.

9. A method of modifying an existing urea plant, said plant comprising a synthesis and recovery section (A), an evaporation section (B), a finishing section (C), a dust scrubbing section (D) and a condensation section (E),
    wherein said synthesis and recovery section (A) is in fluid communication with said evaporation section (B),
    wherein said evaporation section (B) is in fluid communication with said finishing section (C) and has a gas flow line to a condensation section (E);
    wherein said finishing section (C) has a gas flow line to a dust scrubbing section (D), wherein the dust scrubbing section (D) comprises at least one venturi scrubber (F), wherein the method comprises installing a quenching system (G) between the finishing section (C) and the at least one venturi scrubber (F), wherein said quenching system is in fluid communication with a gas flow line from the finishing section (C) and with a gas flow line to venturi scrubber (F) comprised in the dust scrubbing section (D).

10. A method according to claim 9, wherein the method comprises installing one or more venturi scrubbers in parallel to the already present venturi scrubber.

11. The method of modifying an existing urea plant according to claim 10,
- wherein the at least one venturi scrubber is configured for subjecting the quenched off-gas to scrubbing to give scrubbed gas,
- wherein said venturi scrubber comprises a throat, a converging section, and an entrance to said converging section,
- wherein said venturi scrubber is furthermore configured for adding a scrubbing liquid to the venturi scrubber at said throat or at said entrance such that said added scrubbing liquid enters the quenched off-gas
- wherein said quenching system is configured for subjecting the off-gas to quenching with water optionally in the form of an aqueous solution so as to produce quenched off-gas,
- wherein the quenching system is arranged upstream of the venturi scrubber such that the quenching takes place before the off-gas enters the venturi scrubber, and
- wherein the finishing equipment further comprises a washing section comprising an inlet for a washing liquid and configured for percolation of the washing liquid down through said washing section thereby collecting particles from said quenched off-gas stream.

12. A method according to claim 9, wherein the plant further comprises an acid scrubber for the removal of ammonia downstream of the dust scrubbing section.

13. A method according to claim 9, wherein the venturi scrubber is of the micro mist venturi (MMV) type.

* * * * *